United States Patent [19]

Jennings et al.

[11] Patent Number: 5,683,699

[45] Date of Patent: Nov. 4, 1997

[54] MENINGOCOCCAL POLYSACCHARIDE CONJUGATE VACCINE

[75] Inventors: Harold J. Jennings, Gloucester; Francis Michon, Ottawa, both of Canada

[73] Assignee: National Research Council of Canada, Ottawa, Canada

[21] Appl. No.: 485,623

[22] Filed: Jun. 7, 1995

Related U.S. Application Data

[62] Division of Ser. No. 238,600, May 5, 1994, Pat. No. 5,576,002, which is a continuation of Ser. No. 956,830, Oct. 5, 1992, abandoned, which is a continuation of Ser. No. 448,195, Dec. 14, 1989, abandoned.

[51] Int. Cl.$^6$ .................... A61K 39/385; A61K 39/116; C07K 17/10; C08B 37/00
[52] U.S. Cl. .................... 424/197.11; 424/193.1; 424/203.1; 530/403; 530/405; 530/409; 530/411; 536/55.1; 536/18.7
[58] Field of Search .................... 424/197.11, 203.1, 424/193.1, 250.1, 257.1, 137.1; 536/17.2, 18.7, 55.2; 530/403, 405, 409, 411

[56] References Cited

U.S. PATENT DOCUMENTS

| | | |
|---|---|---|
| 4,057,685 | 11/1977 | McIntire . |
| 4,356,170 | 10/1982 | Jennings et al. . |
| 4,619,828 | 10/1986 | Gordon . |
| 4,644,059 | 2/1987 | Gordon . |
| 4,673,574 | 6/1987 | Anderson . |
| 4,695,624 | 9/1987 | Marburg et al. ............. 530/395 |
| 4,727,136 | 2/1988 | Jennings et al. . |

FOREIGN PATENT DOCUMENTS 0 098 581 A3  1/1984  European Pat. Off. .

OTHER PUBLICATIONS

Apicella, The Journal of Infectious Diseases 140(1): 62–72 (1979), "Lipopolysaccharide–Derived Serotype Polysaccharides from *Neisseria meningitidis* Group B".

Bundle, The Journal of Biological Chemistry 249(15): 4797–4801 (1974), "Studies on the Group–Specific Polysaccharide of *Neisseria meningitidis* Serogroup X and an Improved Procedure for its Isolation".

Finne et al., The Lancet, Saturday 13 Aug. 1983, "Antigenic Similaritites Between Brain Components and Bacteria Causing Meningitis".

Chemical Abstracts 109: 134961 for Jennings et al. U.S. Patent No. 4,727,136.

Jennings et al., The Pathogenic Neisseriae, Proceedings of the Fourth International Symposium, Asilomar, California, 21–25 Oct. 1984, pp. 628–632: "Enhancement of the Immune Response to the Group B Polysaccharide of *Neisseria meningitidis* by Means of Its Chemical Modification".

Chemical Abstracts 104: 127835 for above Jennings et al. article from Pathog. Neisseriae, Proc. Int. Symp., 4th (1985), Meeting Date 1984, 628–632.

Jennings et al., The Journal of Immunology 134(4): 2651–2657 (1985), "Determinant Specifications of the Groups B and C Polysaccharides of *Neisseria meningitidis* ".

Jennings et al., The Journal of Immunology 137(5): 1708–1713 (1986), "Induction of Meningococcal Group B Polysaccharide–Specific IgG Antibodies in Mice by Using and N–Propionylated B Polysaccharide–Tetanus Toxoid Conjugate Vaccine".

Chemical Abstracts 105: 170170 for above Jennings et al. article from J. Immunol. (1986), 137(5), 1708–13.

Jennings et al., The Journal of Immunology 142(10): 3585–3591 (1989), "Unique Intermolecular Bactericidal Epitope Involving the Homosialopolysaccharide Capsule on the Cell Surface of Group B *Neisseria meningitidis* and *Escheria coli* K1".

Jennings et al., J. Exp. Med. 165: 1207–1211 (1987): "N–Propionylated Group B Meningococcal Polysaccharide Mimics a Unique Epitope on Group B *Neisseria menningitidis* ".

Lifely et al., Carbohydrate Research 107: 187–197 (1982), "Formation and Identification of Two Novel Anhydro Compounds Obtained by Methanolysis of N–Acetylneuraminic Acid and Carboxyl–Reduced, Meningococcal B Polysaccharide".

Lifely et al., Carbohydrate Research 134: 229–243 (1984), "Rate, Mechanism, and Immunochemical Studies of Lactonisation in Serogroup B and C Polysaccharides of *Neisseria meningitidis* ".

Lifely et al., Carbohydrate Research 156: 123–135 (1986), "Analysis of the Chain Length of Oligomers and Polymers of Sialic Acid Isolated From *Neisseria meningitidis* Group B and C and *Escherichia coli* K1 and K92".

Marburg et al., J. Am. Chem. Soc. 108: 5282–5287 (1986), "Biomolecular Chemistry of Macromolecules: Synthesis of Bacterial Polysaccharide Conjugates with *Neisseria meningitidis* Membrane Protein".

*Primary Examiner*—Ponnathapura Achutamurthy
*Attorney, Agent, or Firm*—Morgan & Finnegan, L.L.P.

[57] ABSTRACT

*Neisseria meningitidis* group B polysaccharide (GBMP) modified by having sialic acid residue N-acetyl groups replaced by N-acyl groups exhibits enhanced immuno response thereto. In addition, induction of antibodies which cross-react with unmodified group B meningococcal and *E. coli* K1 capsular polysaccharide and other tissue cells having a common epitope is minimized. Conjugation of the modified polysaccharides with a physiologically acceptable protein such as tetanus toxoid induces the production of specific protective antibodies with negligible levels of GBMP-cross reactive antibodies, to thereby afford protection against infections caused by group B meningococci and *E. coli* K1.

9 Claims, No Drawings

MENINGOCOCCAL POLYSACCHARIDE CONJUGATE VACCINE

This is a divisional of application Ser. No. 08/238,600, filed May 5, 1994, which is issued on Nov. 19, 1996 as U.S. Pat. No. 5,576,002, which is a continuation of application Ser. No. 07/956,830, filed Oct. 5, 1992, now abandoned, which is a continuation of application Ser. No. 07/448,195, filed Dec. 14, 1989, now abandoned.

The present invention is directed to chemically-modified group B polysaccharides of Neisseria meningitidis. The invention also provides vaccines in which the respective modified polysaccharides are conjugated to a protein carrier.

BACKGROUND OF THE INVENTION

Meningitis caused by group B $N$. meningitidis and $E$. coli K1 remain major world health problems. Group B meningitis occurs in both endemic and epidemic situations and accounts for approximately half of all recorded cases of meningococcal meningitis, while K1-positive $E$. coli are the leading cause of meningitis in neonates. Currently there is no vaccine commercially available against disease caused by group B meningococci and $E$. coli K1. This is in large part due to the fact that the group B meningococcal polysaccharide (GBMP) is only poorly immunogenic in humans. There are some recently reported candidate vaccines based on complexes of the GBMP with outer membrane proteins, but, as yet, there is no clear evidence of their efficacy in humans.

Recently, a new concept of a vaccine based on a synthetic chemically modified (N-propionylated) group B polysaccharide-protein (N-Pr-GBMP-protein) conjugate has been developed. The vaccine induces in mice high titers of IgG antibodies which are not only protective, but also cross-react with unmodified GBMP (i.e. N-acetyl-GBMP). This concept is described and claimed in U.S. Pat. No. 4,727,136, issued Feb. 23, 1988 to Harold J. Jennings et al.

It has been inferred that a vaccine which raises cross-reactive antibodies such as that described in U.S. Pat. No. 4,727,136 could only be successful at the expense of breaking immune tolerance. This hypothesis is legitimized by the identification of a common epitope consisting of a chain of α(2–8)-linked sialic acid residues (with a minimum requirement of ten residues) in both the native N-Ac-GBMP and in human and animal tissue (Jennings, Contrib. Microbiol. Immunol. Basel, Karger, 1989, Vol. 10, 151–165). These polysialosyl chains function as developmental antigens and have for the most part been associated with the fetal state in embryonic neural cell adhesion (Finne et al, Biochem. Biophys. Res. Commun., 1983, 112, 482). During post-natal maturation, this antigen is down-regulated (Friedlander et al, J. Cell Biol. 1985, 101, 412) but is expressed in mature humans during the regeneration of diseased muscles (Cashman et al, Ann. Neuron., 1987, 21, 481) in tumor cells (Roth et al, Proc. Natl. Acad. Sci., 1988, 85, 299) and in natural killer (NK) and CD3+T cells (Husmann et al, Eur. J. Immunol., 1989, 19, 1761. Although the consequences of breaking tolerance to these fetal antigens have not yet been established, it is generally conceded that, because of this cross-reaction, the N-Pr-GBMP-protein conjugate would be severely scrutinized by licensing agencies, resulting in considerable expense and delays because of the complex experimentation necessary to prove the safety of the vaccine before its approval for commercial marketing.

It is an object of the present invention to develop a vaccine having immunogenic properties which are enhanced as compared to those of the N-Pr-GBMP-protein. It is also an object of the invention to provide a vaccine which exhibits substantially reduced cross-reactivity with GBMP.

SUMMARY OF THE INVENTION

In one aspect of the present invention, there is provided a modified B polysaccharide of Neisseria meningitidis having sialic acid residue N-acetyl ($C_2$) groups replaced by a $C_4$–$C_8$ acyl group.

In another aspect, there is provided an antigenic conjugate comprising the N—$C_4$–$C_8$ acyl polysaccharide conjugated to an immunologically suitable protein, having enhanced immunogenicity with substantially reduced inducement of cross-reactive antibodies.

In a further aspect, there is provided a vaccine comprising the N—$C_4$–$C_8$acyl polysaccharide-protein conjugate in association with a suitable carrier or diluent. The vaccines of the invention may also comprise a therapeutically effective amount of an adjuvant suitable for human use, for example aluminum phosphate or aluminum hydroxide.

In a yet further aspect, there is provided a method of immunizing mammals against $N$. meningitidis and $E$. coli K1 infections, which method comprises administering parenterally to mammals subject to such infections, including humans, an immunologically effective amount of the vaccine of the invention. The vaccine is typically administered in an amount of about 1 to 50 micrograms per kilogram body weight, for example 5 to 25, micrograms per kilogram body weight.

In yet another aspect, the invention provides a gamma globulin fraction capable of protection against meningitis caused by Group B $N$ meningitidis and $E$. coli K1. The fraction is produced by immunizing a mammal with a vaccine of the invention. The fraction is then administered to an individual to provide protection against or to treat on-going infection caused by the above organisms. From this, it will be appreciated that the immunogenic vaccine conjugates of the invention will provide for a source of therapeutic antiserum in light of their favorable immunogenicity with minimal inducement of GBMP cross-reactive antibodies. The conjugates of the invention will also be useful for raising monoclonal antibodies and, possibly, antidiotype antibodies.

It has been found in our recent experiments that most of the bactericidal and protective antibodies induced by the N-Pr-GBMP-protein conjugate described in the above-referred to Jennings et al U.S. Pat. No. 4,727,136 are not associated with the GBMP cross-reactive antibodies. In fact, most of the protective activity is contained in an N-Pr-GBMP-specific antibody population which does not cross-react with GBMP. In light of this, it is believed that the N-Pr-GBMP mimics a unique bactericidal epitope on the surface of group B meningococci.

The present invention is based on the discovery that it is possible to synthesize chemically modified GBMP's which mimic the bactericidal epitope and which, in their conjugated form, not only exhibit enhanced immunogenicity but also avoid substantially the inducement of antibodies that cross-react with GBMP.

In arriving at the present invention, a number of different chemically modified GBMP's have been synthesized and conjugated individually to protein, followed by injection of the conjugates into mice and the effects compared to those produced by the N-Pr-GBMP protein conjugate. Surprisingly, it has been found that the N—$C_4$–$C_8$ acyl GBMP-protein conjugates, for example the n-butanoyl, iso-butanoyl, n-pentanoyl, iso-pentanoyl, neo-pentanoyl, hexanoyl, heptanoyl, and octanoyl, and especially the N-butanoyl (N-Bu) GBMP-protein conjugate, substantially mimic the bactericial epitope with substantially reduced inducement of cross-reactive antibodies.

DETAILED DESCRIPTION OF THE INVENTION

The group B meningococcal polysaccharide is isolated from *N. meningitidis* by methods which are known in the art. In one such method, group B meningococci (strain 981B) were grown at 37° C. in a fermenter using 30 g. of dehydrated Todd Hewitt Broth (Difco Laboratories, Detroit, Mich.) per liter of distilled water. Prior to fermenter growth, the lyophilized strain was grown initially in a candle jar at 37° C. on 5% (v/v) Sheeps' Blood Agar (Difco Laboratories, Detroit, Mich.) plates. The bacteria were then transferred to 1.0 liter of Todd Hewitt Broth (as above) in an Erlenmeyer flask which was shaken at 37° C. for 7 hours at 190 r.p.m. This inoculum was then transferred to the fermenter. After fermenter growth (16 hours) the bacteria were killed by the addition of formalin to a final concentration of 0.75%. The bacteria were removed by continuous centrifugation and the group B meningococcal polysaccharide was isolated from the supernatant and purified essentially as described by Bundle et al, *J. Biol. Chem.*, 249, 4797–4801 (1974) except that the protein was extracted by stirring a solution of the crude polysaccharide with cold (4° C.) 9% phenol instead of hot (50°–60° C). This latter process ensures that a high molecular weight form of the GBMP is produced.

*E. coli* (018:K1:H7) (NRCC 4283) were grown at 37° C. in a fermenter in distilled water containing dehydrated Brain Heart Infusion (BHI; 37 g/liter) (Difco Laboratories, Detroit, Mich.). Prior to fermenter growth, the lyophilized strain was grown on 50 ml of BHI solution (same as above) in an Erlenmeyer flask which was shaken at 37° C. for 7 hours at 200 r.p.m. This growth was then transferred to 1.5 liters of BHI (as above) and grown under the same conditions as described above for 7 hours. The inoculum was then transferred to the fermenter.

The procedures employed in the isolation and purification of the capsular polysaccharide of *E. coli* K1 were identical to those described above for the isolation of the group B meningococcal polysaccharide.

It will be appreciated that the isolation and purification procedures described above are not the only ones which may be utilized, and that other published procedures are available, for example those described by Watson et al, *J. Immunol.*, 81, 331 (1958) and in the above-mentioned U.S. Pat. No. 4,727,136.

The native polysaccharide is N-deacetylated to provide a reactive amine group in the sialic acid residue parts of the molecule. The N-deacetylation can be carried out by any known method, for example in a basic aqueous medium at elevated temperatures, for example about 90° to 110° C., and at a pH of about 13 to 14. The basic aqueous medium is suitably an aqueous alkali metal hydroxide solution, for example sodium hydroxide of about 2M concentration. Alternatively, hydrazine in aqueous solution may be used. The degree of N-deacetylation may vary from about 30% to 100%, depending on the conditions. It is preferred to achieve about 90 to 100% N-deacetylation. N-deacetylated product can be recovered for example by cooling, neutralizing, purification if desired, and lyophilization.

Prior to the N-deacetylation procedure, the native polysaccharide has an average molecular weight in the region of about 500,000 to 800,000 Daltons. As a result of N-deacetylation, fragments of the polysaccharide are produced having an average molecular weight ranging from about 10,000 to 50,000 Daltons.

The N-deacetylated polysaccharide fragments are then N-acylated to produce the corresponding N-acylated product. The N-acylation may be carried out by dissolving the N-deacetylated polysaccharide in an aqueous medium having a pH of about 7.5 to 9.0, followed by adding the appropriate acyl anhydride, optionally with an alcohol to increase solubility, and cooling to below 10° C. until the reaction is complete. The reaction medium can be purified, if desired, for example by dialysis, and the N-acylated product then recovered, typically by lyophilization. The reaction is substantially complete within about 10 to 20 hours. The degree of N-acylation, as measured by analytical techniques, typically $^1H$ nmr, is at least 90%, and likely close to 100%. The N-acylation reaction does not result in any significant molecular weight reduction of the fragments.

It is preferred, according to the present invention, to select, for conjugation purposes, the N-acylated material having an average molecular weight corresponding to about 30 to 200 sialic acid residues. This is generally achieved by way of gel filtration of the N-acylated GBMP using an Ultragel (trademark) AcA 44 (Bead diameter 60–140 um) column, using PBS as eluant. Alternatively, a suitable sizing membrane may be employed.

N-acylated material of average molecular weight of 10,000 to 40,000 Daltons, for example 10,000 to 15,000 Daltons, is employed for the invention. This is obtained by collecting the fractions of the eluate of the column containing N-acylated GBMP material having that average molecular weight range. N-acylated material of higher average molecular weight, for example in the region of 30,000 to 40,000 Daltons, has also proved to be useful according to the invention.

The vaccines of the invention are produced by conjugating the N-acylated polysaccharide with an immunologically suitable carrier protein. Preferably, the carrier protein itself is an immunogen. Examples of suitable carrier proteins are tetanus toxoid, diphtheria toxoid, cross-reacting materials (CRMs), preferably $CRM_{197}$, obtained from Sclavo Ltd., Siena, Italy, and bacterial protein carriers, for example meningococcal outer membrane proteins.

Any mode of conjugation may be employed to conjugate the modified polysaccharide fragments with the carrier protein. A preferred method is that described in U.S. Pat. No. 4,356,170, i.e. by introducing terminal aldehyde groups (via oxidation of cis-vicinal hydroxyl groups) into the N-acylated polysaccharide and coupling the aldehyde groups to the protein amino groups by reductive amination. The polysaccharide and the protein are thereby linked through a $—CH_2—NH$-protein linkage.

It is to be understood, however, that the conjugate vaccines of the invention are not limited to those produced via reductive amination. Thus, the vaccines may also be produced by conjugating the N-acylated polysaccharide with the carrier protein using an adipic dihydrazide spacer, as described by Schneerson, R., et al, Preparation, Characterization and Immunogenicity of Haemophilus influenzae type b Polysaccharide-Protein Conjugates, *J. Exp. Med.*, 1952, 361–476 (1980), and in U.S. Pat. No. 4,644,059 to Lance K. Gordon. Alternatively, there may be used the binary spacer technology developed by Merck, as described by Marburg, S., et al, "Biomolecular Chemistry of Macromolecules: Synthesis of Bacterial Polysaccharide Conjugates with *Neisseria meningitidis* Membrane Protein", *J. Am. Chem. Soc.*, 108, 5282–5287 (1988) or, possibly, the reducing ends methodology, as referred to by Anderson in U.S. Pat. No. 4,673,574.

The resulting N-acylated polysaccharide-protein conjugates do not possess significant cross-linking and are soluble in aqueous solutions. This makes the conjugates of the invention good candidates for vaccine use.

The resulting N-acylated-polysaccharide-protein conjugates of the invention have been tested in vitro tests in mice, and have generally been shown to possess improved immunogenic properties as compared with the N-propionylated-polysaccharide. In addition, substantially reduced formation of cross-reactive antibodies is observed. In light of this, it is believed that the vaccines of the invention will be useful against meningitis caused by group B *N meningitidis* or by *E. coli* K1 organisms. Of particular interest are vaccines for protecting human infants who are most susceptible to bacterial meningitis.

The vaccines of the invention are typically formed by dispersing the conjugate in any suitable pharmaceutically acceptable carrier, such as physiological saline or other injectable liquids. The vaccine is administered parenterally, for example subcutaneously, intraperitoneally or intramuscularly. Additives customary in vaccines may also be present, for example stabilizers such as lactose or sorbitol and adjuvants such as aluminum phosphate, hydroxide, or sulphate.

A suitable dosage for the vaccine for human infants is generally within the range of about 5 to 25 micrograms, or about 1 to 10 micrograms per kilogram of body weight.

EXAMPLES

The invention is illustrated by the following non-limiting examples. The N-acetyl, N-propionyl, N-butanoyl, N-isobutanoyl, N-pentanoyl and N-hexanoyl-GBMP-protein conjugates have been prepared for evaluation purposes, and the results are discussed in the examples.

MATERIALS AND METHODS FOR PREPARING CONJUGATES (a) Materials

Propionic, butanoic, isobutanoic, pentanoic, and hexanoic anhydrides together with colominic acid were obtained from Sigma Chemicals Co., St. Louis, Mo. Because colominic acid is structurally identical to the group B meningococcal polysaccharide (GBMP), it is referred to henceforth as GBMP. Tetanus toxoid (TT) was obtained from the institut Armand Frappier, Laval, Quebec, and its monomeric form, used in all the conjugations, was obtained by passage of the above preparation through a Bio-Gel (trademark) A 0.5 (200–400 mesh) column (1.6×90 cm) (Bio-Rad, Richmond, Calif.), equilibrated and eluted with 0.01M phosphate buffered physiologic saline (PBS) (pH 7.4)

(b) N-Deacetyation of the GBMP

The GBMP (Na$^+$ salt) (1.0 g) was dissolved in 5 ml of 2M NaOH and, following the addition of NaBH$_4$ (150 mg), the solution was heated at 110° C. for 6 hours in a screw cap Teflon (trademark) container (60 mL). This procedure is essentially as described in *J. Immunol.*, 134, 2651 (1985) and U.S. Pat. No. 4,727,136, both in the name of Harold J. Jennings, et al. The cooled diluted solution was then exhaustively dialyzed against distilled water at 4° C., and lyophilized. The fact that N-deacetylated GBMP was obtained was determined by the absence of the methylacetamido signal (singlet at delta 2.07) in the $^1$H-nmr spectrum of the N-deacetylated GBMP.

(c) N-Acylations of the GBMP

N-Deacetylated GBMP (1.0 g) was dissolved in 50 mL of 5% aqueous NaHCO$_3$. To five individual aliquots (10 mL of the above solution) were added either propionic, butanoic, isobutanoic, pentanoic or hexanoic anhydrides. These reagents were added in 3×0.5 mL aliquots over a 3 hour period of time at room temperature while the solution was maintained at pH 8.0 with 0.5N NaOH. Methanol (0.5 mL) was added simultaneously with each addition of anhydride in order to increase their solubility. Finally the solutions were stirred for 16 hours at 4° C., exhaustively dialysed against distilled water at 4° C., and lyophilized. The individual N-propionylated, N-butanoylated, N-isobutanoylated, N-pentanoylated and N-hexanoylated GBMP were all obtained in yields in excess of 90%. In each case, essentially complete N-acylation was confirmed by the disappearance in the respective $^1$H-nmr spectrum of N-deacetylated GBMP.

(d) Sizing of the Fragments of the Different N-acylated GBMP

Gel filtration, using an Ultragel (trademark) AcA 44 (bead diameter 60–140 μm) column (IBF Biotechnics, Savage, Md.) employed to obtain the desired average molecular weight N-acylated GBMP material. Fractions eluting from the column at $K_D$ 0.5 to $K_D$ 0.7 as measured by FLPC (see below) were collected, dialyzed, and lyophilized. This range of $K_D$ values corresponds to N-acylated GBMP of approximately 30–50 sialic acid residues (10,000 to 15,000 Daltons, typically 12,000 Daltons average molecular weight). Fractions in the range of $K_D$ 0.2 to 0.4 corresponding to fragments having an average molecular weight in the range of 30,000 to 40,000 Daltons have also been collected and conjugated. Thus, N-acylated material eluting in the $K_D$ range of 0.2 to 0.7 is of particular interest.

(e) Polysaccharide Conjugates

Terminal aldehyde groups were introduced into the N-acylated GBMP by periodate oxidation (see U.S. Pat. No. 4,356,170). The N-acylated GBMP fragments above were oxidized in 0.1M aqueous NaIO$_4$ (sodium metaperiodate) (10 mL) for 2 hours at room temperature in the dark. Excess periodate was then destroyed by the addition of 1 mL of ethylene glycol and the solution was then exhaustively dialyzed at 4° C, and lyophilized. The use of NaBH$_4$ in the N-deacetylation procedure (except for the GBMP) results in the transformation of the terminal reducing sialic acid residues of each of the N-acylated GBMP, to open chain polyol residues. This type of residue is periodate sensitive (see *J. Immunol.*, 127, 1011 (1981) and U.S. Pat. No. 4,356,170 Harold J. Jennings et al), thereby resulting in the introduction of aldehyde groups into the N-acylated GBMP fragments at both termini.

The oxidized fragments (100 mg) were dissolved in 0.1M NaHCO$_3$ (pH 8.1) buffer (2 mL) and TT (20 mg) was added to the solution. Finally, following the addition of sodium cyanoborohydride (NaCNBH$_3$) (40 mg), the solution was gently stirred at room temperature. The course of the conjugation was followed by FPLC using a gel filtration column containing SUPEROSE (trademark) 12 HR10/30 (Pharmacia), run isocratically at 1 mL/min in PBS buffer at pH 7.2, both the protein and N-acylated GBMP fragments being monitored at 214 nm. The fragments had $K_D$ 0.6, TT had $K_D$ 0.39 and the conjugates had $K_D$ 0.23. The conjugation was complete when all the TT was expended as determined by the loss of the peak in the FPLC chromatogram corresponding to the component at $K_D$ 0.39. In most cases, the conjugations were complete in 2 days but were left for a total reaction time of 4 days. The potential unreacted aldehyde groups were finally reduced with sodium borohydride (20 mg) prior to gel filtration.

The polysaccharide—TT conjugates were separated from the polysaccharide fragments by gel filtration using a Bio Gel A column with PBS as eluant. The eluant containing the conjugate was dialyzed against distilled water and lyophilized. The N-acylated GBMP—TT conjugates contained from 12–30%, typically 12–20%, sialic acid as determined by the resorcinol method described by Svennerholm, L., Quantitative Estimation of Sialic Acids, II A Colorimetric Resorcinol-Hydrochloric Acid Method, *Biochim. Biophys. Acta.* 24, 604 (1957). This indicates that the conjugates had a molar ratio of polysaccharide to TT of 2–3:1 respectively.

IMMUNIZATION AND IMMUNOASSAYS (a) Immunization Procedures

Twenty female white CFI mice (8–10 weeks old) were immunized intraperitoneally (3 times at 3 week intervals) with each individual N-acylated GBMP-TT conjugate in Freunds' complete adjuvant (FCA) (Difco, Detroit, Mich.). Each immunization contained sufficient conjugate (10–12 µg) to contain 2 µg of sialic acid. Eleven days after the third injection, the mice were exsanguinated. The following tests were done on the sera.

(b) Radioactive Antigen Binding Assay

This assay was carried out by a modification of the Fart technique using extrinsically [$^3$H]-labeled GBMP (Jennings H. J., et al, Determinant Specificities of the Groups B and C polysaccharides of *Neisseria meningitidis*, *J. Immunol.*, 134, 2651 (1985), or [$^3$H]-labeled N-Pr-GBMP (Jennings H. J., et al, Unique Intermolecular BaCtericidal Epitope involving the Homo-Sialo Polysaccharide Capsule on the Cell Surface of Group B *Neisseria meningitidis* and *Escherichia coli* K1, *J. Immunol.*, 142, 3585–3591 (1989). The reaction mixture for the radioactive antigen-binding assay was obtained by mixing in Eppendorf polypropylene micro test tubes 20 uL of pooled antisera, from groups of 20 mice immunized with each individual N-acylated GBMP-TT conjugate, diluted to 100 µL with PBS, with [$^3$H]-labeled GBMP and [$^3$H]-labeled N-Pr-GBMP in 50 µL of PBS. After incubation at 4° C. for 16 hours, 150 µL of saturated (at 4° C.) ammonium sulfate (pH 7.0) was added to the tubes and the tubes agitated and left to stand at 4° C. for 30 min. The tubes were centrifuged at 15,000 rpm for 10 min. and two aliquots of 130 µL were drawn from the tubes. The aliquots were mixed with 2 mL of water and a scintillant-containing xylene (ACS aqueous scintillant) and the mixtures were counted in a liquid scintillation counter. Results are given in Table 1.

TABLE 1

Binding of [$^3$H] - labeled - N—Ac—GBMP to different mouse anti- N—acyl—GBMP—TT conjugate sera.

| Antiserum | % Binding* | | | |
|---|---|---|---|---|
| | 1 | 2 | 3 | 4 |
| N—Pr—GBMP—TT | 41 | 40 | 39 | 12 |
| N—Bu—GBMP—TT | 4 | 4 | 7 | 4 |
| N—IsoBu—GBMP—TT | 9 | — | — | — |
| N—Pen—GBMP—TT | 36 | — | — | — |
| N—Hex—GBMP—TT | 16 | — | — | — |

*The four binding experiments were carried out on pooled antisera from 20 immunized mice.
Abbreviations used in Table 1 and other tables: N—Ac—, N—Pr, N—Bu, N—IsoBu, N—Pen, N—Hex— stand for N—Acetyl, N—Propionyl—, N—Butanoyl—, N—Isobutanoyl—, N—Pentanoyl— and N—Hexanoyl—.

The numerals 1, 2, 3 and 4 are results of four repeat experiments. Table 1 demonstrates conclusively that the N-Ac-GBMP (which carries the same epitope as fetal N-CAM) binds less to the antiserum induced by the N-Bu-GBMP, N-IsoBu-GBMP, N-Pen-GBMP and N-Hex-GBMP than that induced by the N-Pr-GBMP. From this, it can be deduced from Table 1 that the N-Bu-, N-IsoBu, N-Pen- and N-Hex-polysaccharide-conjugates raise less cross-reactive antibodies than the N-Pr-conjugate.

(c) Quantitative Precipitin Analyses

These experiments were carried out by the method of Kabat and Mayer, Experimental Immunochemistry Charles C. Thomas, Springfield, p.22 (1961). Aliquots (100 µL) of anti-N-acyl GBMP-TT sera (diluted 5 fold in PBS) were reacted in tubes with increasing concentrations of the N-acetyl (colominic acid), N-propionyl, N-butanoyl, N-isobutanoyl, N-pentanoyl and N-hexanoyl GBMP in a total volume of 200 µL (adjusted with PBS). The higher molecular weight fractions of these derivatives were used in these experiments and they were obtained from the eluate of the Ultragel AcA 44 column ($K_D$ 0.4 as measured by FPLC) previously used to size the fragments of the N-acylated GBMP. The tubes were incubated at 4° C. for 4 days with daily mixing, centrifuged, and the quantity of antibody protein was determined by the method of Lowry et al, Protein Measurement with the Folin phenol reagent, *J. Biol. Chem.*, 1933, 265 (1951). The results are given in Table 2.

TABLE 2

Precipitation[a] of mouse anti-N—acyl—GBMP—TT sera using different N—acyl GBMP as precipitating antigens.

| Antiserum | N—acyl—GBMP antigen | | | | |
|---|---|---|---|---|---|
| | N—acetyl | N—propyl | N—butyl | N—pentyl | N—hexyl |
| N—Pr—GBMP—TT | 0.16 | 0.40 | 0.20 | 0.15 | 0.15 |
| N—Bu—GBMP—TT | 0.04 | 1.15 | 2.60 | 3.20 | 1.90 |
| N—Pen—GBMP—TT | 0.13 | 0.38 | 0.44 | 6.35 | 3.55 |
| N—Hex—GBMP—TT | 0.02 | 0.08 | 0.80 | 4.15 | 4.40 |

[a]Maximum amount of antibody precipitated expressed in mg/mL of antiserum

As regards cross-reactivity, the first column of Table 2 indicates that very little cross-reactive antibodies are produced by the N-Bu and N-Hex conjugates as compared to the N-Pr conjugate. It can also be seen that the N-Pen conjugate produces less cross-reactive antibodies than the N-Pr conjugate.

With reference to immunogenicity, in terms of homologous response, it can be seen from Table 2 that the N-Bu- (2.60), N-Pen- (6.35) and N-Hex- (4.40) GBMP-TT conjugates are more immunogenic than the N-Pr-GBMP analog (0.40).

(d) ELISA

The wells of EIA microtitration plates (Flow Labs, Mississauga, Ontario, Canada) were coated with a 10 μg/mL solution of either GBMP-, NPrGBMP- or NBu-GBMP-BSA conjugates in PBS (100 μL/well). The plates were left for 18 hours at 4° C. and after coating they were washed with 1% bovine serum albumin in PBS for 10 min. at room temperature (blocking step). The wells were then filled with 100 μL of serial 10-fold dilutions in PBS of anti-mouse-N-acyl GBMP-TT conjugate sera and the plates were incubated for 1 hour at room temperature. After washing with SBT the plates were incubated for 1 hour at room temperature with 50 μL of the appropriate dilution of goat antimouse immunoglobulin peroxidase labeled conjugates (Kirkegard and Perry Laboratories), then the contents of the wells were aspirated and the plates washed five times with SBT. Finally 50 μL of Tetramethylene blue-peroxidase substrate (TMB) (Kirkegard and Perry Laboratories) were added to each well after 10 min the absorbance at 450 nm was measured with a Multiscan spectrophotometer (Flow Laboratories, Mississauga, Ont.). Results are given in Table 3.

With reference to cross-reactivity, it can be seen from Table 3 that the N-Bu-GBMP-TT conjugate raises less cross-reactive antibodies with respect to N-Ac-GBMP (1000) than does the N-Bu-GBMP-TT conjugate (7800). The reason for this is that the GBMP binds less to antibody induced by the N-Pr-GBMP-TT conjugate than that induced by the N-Pr-GBMP-TT conjugate. Similar comments apply with respect to the N-IsoBut-GBMP-TT conjugate.

As regards immunogenicity, the N-Bu conjugate is more immunogenic than the N-Pt analogue, as shown by the homologous binding titers of 52,000 (N-Bu) and 40,000 (N-Pr).

(e) Radioactive Binding Inhibition Assay

Increasing concentration of the larger molecular sized N-acyl GBMP inhibitor in PBS (80 μL) were added to 20 μL of mouse anti-N-Pr-GBMP-TT conjugate antiserum, an amount sufficient to bind 50% of the ($^3$H)-labeled N-Pr-GBMP in the absence of inhibitor. The tubes were incubated for 1 hour at 37° C. and 50 μL of ($^3$H)-labeled N-Pr-GBMP in PBS was added. After gentle mixing the tubes were incubated at 4° C. for 16 hours and the assays were performed exactly as described previously for the radioactive antigen binding assay. The % inhibition was calculated using the following formula:

percent inhibition=100×[(cpm with inhibitor minus cpm without inhibitor)/(cpm without antibody minus cpm without inhibitor)].

TABLE 3

ELISA titrations of pooled mouse anti-N—acyl—GBMP—TT conjugate serum against N—acyl—GBMP—BSA conjugates.

| Coating Antigen | Titers[a] of Antisera | | |
|---|---|---|---|
| | a. N—Pr—GBMP[b] | a. N—Bu—GBMP[b] | a. N—Isobu—GBMP[b] |
| N—Ac—GBMP—BSA | 7800 | 1000 | 7000 |
| N—Pr—GBMP—BSA | 40000 | 39000 | 9800 |
| N—Bu—GBMP—BSA | 26000 | 52000 | 9700 |
| N—IsoBu—GBMP—BSA | — | — | 25000 |

[a]titer (GM) = reciprocal of dilution at 50% of the maximum absorbance at 450 nm.
[b]N—acyl specific antisera induced in mice by homologous N—acyl—GBMP—TT conjugates.

Results are given in Table 4.

TABLE 4

Inhibition of binding of [$^3$H] - labeled N—Pr—GBMP to mouse anti-N—Pr—GBMP—TT conjugate induced $IgG_{2a}$, $IgG_{2b}$ (A)[a] and $IgG_1$ (B)[a] antibodies.

| Inhibitor[b] | A | B |
|---|---|---|
| N—Ac—GBMP | >50.0 | >50.0 |
| N—Pr—GBMP | 0.6 | 0.3 |
| N—Bu—GBMP | 0.3 | 0.2 |
| N—IsoBu—GBMP | >50.0 | — |
| N—Pen—GBMP | 2.3 | 2.5 |
| N—Hex—GBMP | 10.2 | 10.0 |

[a]These were fractions of mouse polyclonal anti-N—Pr—GBMP—TT, serum, described in Jennings et al, J. Immunol., 142, 3585–3591 (1989).
[b]Micrograms of inhibitor to give 50% inhibition.

Bactericidal Assays

These assays were carried out by the method described by Jennings et al., *J. Exp. Med.*, 165, 1207–1211 (1987).

*Neisseria meningitidis* strain B (M 986) was used in these assays. Results are given in Table 5.

TABLE 5

Binding of [$^3$H] - labeled - N—Pr—GBMP to different mouse anti-N—acyl—GBMP—TT conjugate sera and the bactericidal titers of the respective antisera.

| Antiserum | μL of antiserum[a] | Bactericidal Titer[b] |
|---|---|---|
| N—Pr—GBMP—TT | 13 | 128 |
| N—Bu—GBMP—TT | 10 | 64 |
| N—IsoBu—GBMP—TT | ND | 64 |
| N—Pen—GBMP—TT | 24 | 64 |
| N—Hex—GBMP—TT | >100 | 8 |
| N—Ac—GBMP—TT | >100 | 8 |

[a]μL of antiserum (diluted 5 fold with PBS) required for 50% binding.
[b]Dilution experiment: one dilution difference, e.g. 128 compared to 64, is within experimental error.

Table 4 illustrates that N-Bu-GBMP is as good an inhibitor as the N-Pr-GBMP for the binding of the latter to its own homologous antibodies. Therefore, the use of N-Bu-GBMP in place of N-Pr-GBMP does not result in any significant loss of properties exhibited by N-Pr-GBMP. Table 5 demonstrates that the N-Bu-GBMP binds as well as the N-Pr-GBMP to antibodies induced by the N-Pr-GBMP-TT conjugate. Antisera induced by both the N-Bu-GBMP-TT and N-Pr-GBMP-TT conjugates gave similar bactericidal titers. This evidence indicates the equivalence of the N-Bu-, N-IsoBu- and N-Pen-GBMP to the N-Pr-GBMP in their ability to mimic the bactericidal epitope on the surface of the group B meningococci.

We claim:

1. A gamma globulin fraction comprising antibodies directed against group B *N. meningitidis* or *E. coli* K1, said gamma globulin fraction being produced by immunizing a mammal with an antigenic conjugate comprising a modified group B polysaccharide of *Neisseria meningitidis* or *E. coli* K1 having sialic acid N-acetyl residue groups replaced by a N—C4–$C_8$-acyl group conjugated to an immunologically-suitable protein, wherein the the N-acetyl groups are replaced with the N—$C_4$–$C_8$ acyl groups to an extent that when said modified group B polysaccharide is conjugated to said protein the amount of substitution of acyl for acetyl groups is sufficient to reduce the inducement of antibodies which bind native GBMP, compared to the binding of native GBMP to antibodies induced by a N-pr-GBMP-protein conjugate—has been inserted.

2. The gamma globulin fraction according to claim 1, wherein the $C_4$–$C_8$ acyl group of the conjugate used to immunize the mammal is selected from the group consisting of n-butanoyl, isbutanoyl, n-pentanoyl, n-hexyanol, n-heptanoyl and n-octanoyl.

3. The gamma globulin fraction according to claim 1, wherein the $C_4$–$C_8$ acyl group of the conjugate used to immunize the mammal is selected from the group consisting of n-butanoyl, isbutanoyl, n-pentanoyl and n-hexyanoyl.

4. The gamma globulin fraction according to 3, wherein the $C_4$–$C_8$ acyl group of the conjugate used to immunize the mammal is n-butanoyl.

5. The gamma globulin fraction according to claim 4 wherein the protein of the conjugate elicits antibodies to bacteria.

6. The gamma globulin fraction according to claim 5 wherein the protein of the conjugate is selected from the group consisting of tetanus toxoid, diphtheria toxoid, cross-reacting material (CRM) and a meningococcal outer membrane protein.

7. The gamma globulin fraction according to claim 6 wherein the protein and the polysaccharide of the conjugate are covalently linked through a —$CH_2$—NH— linkage and wherein the N of the linkage is contributed by the protein.

8. The gamma globulin fraction according to claim 7 wherein the $C_4$–$C_8$ acyl group of the conjugate is of n-butanoyl.

9. The gamma globulin fraction according to claim 8, wherein the CRM is $CRM_{197}$.

* * * * *